US006167887B1

(12) United States Patent
Clark et al.

(10) Patent No.: US 6,167,887 B1
(45) Date of Patent: Jan. 2, 2001

(54) SELECTED C-10 PERFLUORINATED HYDROCARBONS FOR LIQUID VENTILATION AND ARTIFICIAL BLOOD

(75) Inventors: Leland C. Clark, Cincinnati; Richard E. Hoffmann, Beavercreek, both of OH (US)

(73) Assignee: Synthetic Blood International, Inc., Kettering, OH (US)

(*) Notice: Under 35 U.S.C. 154(b), the term of this patent shall be extended for 0 days.

(21) Appl. No.: 08/975,743

(22) Filed: Nov. 21, 1997

(51) Int. Cl.[7] ................................................. A61B 19/00
(52) U.S. Cl. ..................................... 128/898; 128/200.24
(58) Field of Search ............................. 128/898, 200.24; 514/628, 755

(56) References Cited

U.S. PATENT DOCUMENTS

| | | | |
|---|---|---|---|
| Re. 33,451 | 11/1990 | Clark, Jr. | 514/628 |
| 3,911,138 | 10/1975 | Clark, Jr. | 424/352 |
| 4,453,028 | 6/1984 | Lagow | 570/130 |
| 4,686,024 | 8/1987 | Scherer, Jr. et al. | 204/157.95 |
| 5,300,528 * | 4/1994 | Graybill et al. | 514/772 |
| 5,437,272 | 8/1995 | Fuhrman | 128/203.12 |
| 5,674,913 | 10/1997 | Clark, Jr. | 514/755 |
| 5,840,767 | 11/1998 | Clark, Jr. | 514/759 |

FOREIGN PATENT DOCUMENTS

| | | | |
|---|---|---|---|
| 0521492 | 1/1993 | (EP) | C07C 23/10 |
| 92/19232 | 12/1992 | (WO) | A61K 31/02 |
| 95/31191 | 11/1995 | (WO) | A61K 31/02 |
| 97/19678 | 6/1997 | (WO) | A61K 31/025 |

OTHER PUBLICATIONS

Moore R.E., et al., "Synthesis and Physical Properties of Perfluorocompounds Useful as Synthetic Blood Candidates", Oxygen Carrying Colloidal Blood Substitutes, International Symposium Perfluorochem. Blood Substitutes, 1982, pp. 50–60.

Clark L. et al., "A New Look at the Vapor Pressure Problem in Red Cell Substitutes", Int. Congr. Ser.—Excerpta Med. (1979), 486 (Proc. Int. Symp. Perfluorochem. Blood Substitutes, 4th, 1978), 1979, pp. 55–67.

Chemical Abstracts, vol. 100, No. 3, Jan. 16, 1984, Columbus Ohio, U.S. Abstract No. 17149, Okamoto H. et al., "Fate of perfluorochemical impurities contained in both perfluorodecaline (FDC) and perfluorotripropylamine (FTPA) in rats following intravenous injection of their emulsions".

Smith et al. "Partial Liquid Ventilation: a Comparison Using Conventional and High Frequency Techniques in an Animal Model of Acute Respiratory Failure", *Crit Care Med*, (1997) vol. 25, No. 7: pp. 1179–1186.

Clark, Jr. et al. "Physiological Evaluation of Fluorocarbon Emulsions with Notes on F–Decalin and Pulmonary Inflation in the Rabbit", *Mat. Res. Soc. Symp. Proc.*, (1989), pp. 129–134.

Lin, Wen–Heuy et al., "The Synthesis of Highly Fluorinated Alkylcyclohexanes for Use as Oxygen Carriers and the $^{19}$F $^{13}$C NMR Spectra of Alkylcyclohexanes", Journal of Fluorine Chemistry, 50 (1990) pp. 345–358.

Chemical Abstract, vol. 96, No. 9, Mar. 1, 1982, Abstract No. 68466.

(List continued on next page.)

*Primary Examiner*—Dinh X. Nguyen
(74) *Attorney, Agent, or Firm*—Klein & Szekeres, LLP

(57) ABSTRACT

Perfluorinated alkylcyclohexane and alkyl cyclopentane derivatives of the empirical formula $C_{10}F_{20}$ boil at atmospheric pressure in the range of 144–146° C. and are utilized as mediums for gas transport in liquid ventilation and in artificial blood. Compounds of the $C_{10}F_{20}$ formula which can exist only as a single stereoisomer are preferred as mediums for gas transport.

18 Claims, 1 Drawing Sheet

OTHER PUBLICATIONS

Varushchenko, Raisa M. et al., "Thermodynamics of Vaporization of Some Cyclic Perfluorocarbons", *Fluid Phase Equilibria* vol. 126 (1996) pp. 93–104.

Quintel, M. et al., "Liquid Ventilation with Perfluorocarbons", Anästhesiol. Intensivmed. Notfallmed. Schmerzther, 1996; 31:461–469 (with English abstract).

Shaffer et al. "Liquid Ventilation a State of the Art Review", *Pediatric Pulmonology* 14:102–109 (1992).

Clark Jr. et al. "Response of the Rabbit Lung as a Criterion of Safety for Fluorocarbon Breathing and Blood Substitutes", *Beamed., Art. Cells & Immob. Biotech*, 20(2–4) 1085–1099 (1992).

Clark Jr. et al. "Fluorovent™: a New Perfluorocarbon for Liquid Ventilation", *Symposium Hot Topics '95 in Neonatology*, Dec. 3–5, 1995, Washington D.C.

* cited by examiner

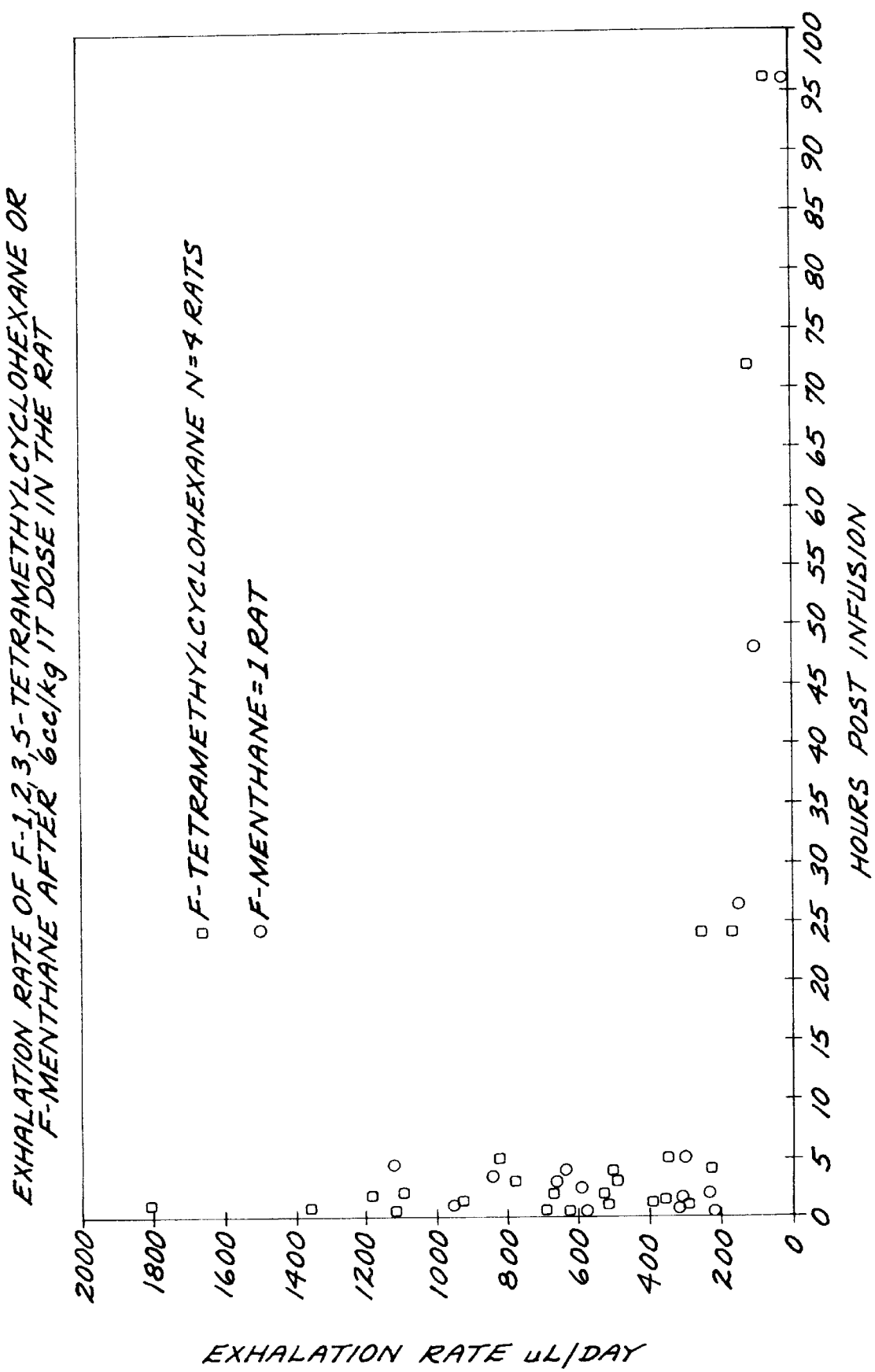

SELECTED C-10 PERFLUORINATED HYDROCARBONS FOR LIQUID VENTILATION AND ARTIFICIAL BLOOD

BACKGROUND OF THE INVENTION

1. Field of the Invention

The present invention is in the field of biological gas exchange in mammals using C-10 perfluorinated hydrocarbons (perfluorocarbons) as a medium of the exchange. More particularly, the present invention is directed to use of those C-10 perfluorinated hydrocarbons in biological gas exchange, primarily in liquid ventilation, which due to their chemical structure can be readily obtained or purified in a state free of isomeric contaminants.

2. Brief Description of the Prior Art

It has been known for a long time that perfluorocarbons are chemically and biologically inert substances and have the unique capability of dissolving very large volumes of gases, including oxygen and carbon dioxide. Taking advantage of these properties of the perfluorocarbons, it was demonstrated as early as 1966 that the lives of experimental animals, such as mice, can be sustained while the animals are submerged in an oxygenated perflurocarbon liquid medium.

The above-noted pioneering discovery spurred extensive further research in this field by the present inventor, his coworkers and by other scientists as well. As a result, perfluorocarbons emerged as leading candidates for gas-transporting components of artificial blood, and as mediums of gas exchange in liquid ventilation.

Specifically, liquid ventilation is a term used for describing gas exchange, i.e. breathing of a mammal, where a certain volume of gas transporting liquid is added to fill the entire or partial volume capacity of the lungs, and where the presence of the liquid facilitates the breathing process. The term "tidal liquid ventilation" or "total liquid ventilation" is used to describe liquid ventilation where the lungs of the mammal are completely filled with the liquid which is oxygenated by bubbling or by passing it through a membrane oxygenator. It is now generally accepted in the art that although the feasibility of using perfluorinated hydrocarbons to sustain the lives of experimental animals was initially demonstrated by this method (the animal was submerged in the liquid medium) "total liquid ventilation" is unlikely to become a medically accepted procedure to be used with humans who need respiratory assistance.

Another form of liquid ventilation where only the functional residual volume of the lung is filled with the perfluorocarbon and where gas exchange is assisted with the use of a mechanical ventilator, is termed "partial liquid ventilation". In partial liquid ventilation approximately 30 milliliters (ml) of the perfluorocarbon (or mixture of perfluorocarbons) is used per kilogram (kg) body weight of the mammal.

Still another form, which has been suggested relatively recently by one of the present inventors is "low volume" or "alveolar" ventilation where the perfluorocarbon (or mixture of perfluorocarbons) is added in sufficient quantity only to fill the alveoli (air sacs) of the lung and the mammal is allowed to breath normally, or with the assistance of a mechanical ventilator. In this "low volume" method only approximately 0.1 to approximately 10 ml of the perfluorocarbon (or mixture of perfluorocarbons) is used per kg body weight of the mammal.

The research prompted by the 1966 discovery of the possibility of "liquid breathing" in a perfluorocarbon medium, resulted in voluminous scientific and patent literature on the medical aspects of the subject. It also led to the development of voluminous literature pertaining to the manufacturing and selecting suitable perfluocarbons for "liquid breathing" and "artificial blood" purposes. A substantial list of scientific papers, publications and patents is provided in an Information Disclosure Statement, which is filed in connection with this application for patent. An article titled "Liquid Ventilation A State of the Art Review" by Shaffer et al. in Pediatric Pulmonology 14:102–109 (1992) reviews the properties of perfluorocarbons which are pertinent to liquid breathing and provides a long list of references pertinent to the subject.

A publication titled "Response of the rabbit lung as a criterion of safety for flurocarbon breathing and blood substitutes" by Clark Jr. et al. in Biomat., Art. Cells & Immob. Biotech 20(2–4) 1085–1099 (1992) describes hyperinflated non-collapsible lung syndrome (HNCL) which has emerged as a serious problem associated with the use of certain perfluorocarbons in liquid breathing and in artificial blood as well. Briefly, it was found in experimental rabbits, and later in other mammals as well, that when perfluorinated decalin (F-decalin) and certain other perfluorocarbons are administered to rabbits either as an emulsion (artificial blood) or by intratracheal infusion, the animals tend to develop hyperinflated non-collapsible lungs, which can eventually prove to be fatal. The hyperinflated non-collapsible lungs are fatal to the animal because, the lobes completely fill the thorax and are not compliant.

The above-noted article in Biomat., Art. Cells J. Immob. Biotech and a poster presented by Clark Jr. et al. at a symposium Hot Topics '95 in Neonatology, Dec. 3–5, 1995, Washington D.C., titled "Fluorovent™: A New Perfluorocarbon for Liquid Ventilation", describe the scientific quest for perfluorocarbons which would be ideally suited for use in liquid ventilation and artificial blood as well. The criteria mentioned for ideal, or at least better suitability is avoidance of hyperinflated lung syndrome and an acceptably low "body dwell time" after administration of the perfluorocarbon liquid to the mammal. Out of an abundance of caution it is considered desirable for the fluorocarbons to be completely removed from the body after treatment. Alternatively, if complete removal after treatment is impossible, it is in any case desired for the perfluorocarbon to have as short a residual dwell time as possible. In this regard it is noted that the primary mechanism by which the mammalian body eliminates fluorocarbons is through exhalation by the lungs. Although the precise mechanism of this removal by exhalation is not presently known the rate of removal has been recognized to be related to the volatility (vapor pressure at body temperature) of the perfluorocarbon liquid. While, as mentioned above, excessive persistence of the perfluorocarbon in the mammalian body after treatment is undesirable, excessive or too rapid loss by exhalation/ evaporation is also undesirable since it requires replenishment of the perfluorocarbon liquid during treatment. As it is readily understood by those skilled in the art, the rate of loss due to exhalation/evaporation is also related to the volatility (vapor pressure at body temperature) of the perfluorocarbon substance.

Finally, as manifested in the above-mentioned article by Clark Jr. et al. in Biomat., Art. Cells & Immob. Biotech 20(2–4) 1085–1099 (1992) and in the Abstract of the poster presentation by Clark Jr. et al. at a symposium Hot Topics '95 in Neonatology, the prior art recognized that causation of hyperinflated non-collapsible lung syndrome (HNCL) is also related to the volatility of the perfluorocarbon liquid, whether it is used in artificial blood or in liquid ventilation. For example, perfluorinated decalin (F-decalin) having a boiling point of 141–142.5° C. is known to cause hyperinflated lung syndrome, while perfluorinated methyldecalin (F-methyldecalin) having a boiling point of 161° C. does not. F-methyldecalin, however, persists somewhat longer in the body than what is considered desirable. Thus, the article in Biomat., Art. Cells & Immob. Biotech 20(2–4) 1085–1099 (1992) refers to a search for flurocarbons "having boiling points between 140° C. and 165° C. "in order to find a perfluorinate with the highest transpiration rate, and hence vapor pressure, compatible with an acceptable body dwell time.". The abstract of the presentation at the above-mentioned symposium refers to an evaluation of the properties of many perfluorocarbons (PFCs) . . . "to find the optimum PFC for liquid ventilation". The abstract mentions "two properties—boiling point related lung hyperinflation and rapid pulmonary exhalation— . . . , as important selection criteria."

As it will become apparent from the ensuing description, the present invention provides perfluorocarbons which avoid the hyperinflated lung syndrome and other problems associated with the prior art, and therefore meet the selection criteria mentioned in the above-quoted abstract. Moreover, still another "important selection criterion" has been discovered in accordance with the present invention, and the perfluorocarbons suggested for use in liquid ventilation and for artificial blood also satisfy the newly suggested criterion.

As further background to the present invention applicant cites:

U.S. Pat. No. Re: 33,451 to one of the present inventors that describes the use of perfluorocarbons as blood substitutes;

U.S. Pat. No. 3,911,138 to one of the present inventors that pertains to the search for perfluorocarbons having ideal balance of properties for use in liquid ventilation;

PCT Patent application No. 92/19232 to Faithful et al. and U.S. Pat. No. 5,437,272 to Fuhrman which pertain to liquid breathing utilizing perfluorocarbons to fill the pulmonary functional residual capacity of the mammal;

A publication by Smith et al. in Crit Care Med 1997 Vol. 25, No. 7 pp1179–1186, titled: Partial liquid ventilation: A comparison using conventional and high frequency techniques in an animal model of acute respiratory failure, and A publication by Clark, Jr. et al. in Mat. Res. Soc. Symp. Proc. Vol. 110 (1989) pp129–134, titled "Physiological evaluation of fluorocarbon emulsions with notes on F-decalin and pulmonary inflation in the rabbit."

SUMMARY OF THE INVENTION

It is an object of the present invention to provide a perfluorocarbon compound, or several perfluoro compounds which are well suited for use as gas exchange medium in liquid ventilation and as gas exchange medium in artificial blood.

More particularly, it is an object of the present invention to provide a perfluorocarbon compound, or several perfluoro compounds which have the appropriate vapor pressure at body temperature so that their use as medium of gas exchange in liquid ventilation or in artificial blood does not cause hyperinflated lung syndrome, and which nevertheless do not unduly persist in the body after treatment or use of the perfluorocarbon is discontinued.

It is a further object of the present invention to provide a perfluorocarbon compound, or several perfluoro compounds which satisfy the foregoing objectives, and which, due to their chemical structure, exist only as single isomers, and can be obtained in a state substantially free of isomeric contaminants.

The foregoing and other objects and advantages of the invention are attained by selecting and utilizing perfluorocarbon compounds as gas exchange medium in liquid breathing and in artificial blood which have the empirical formula $C_{10}F_{20}$, a molecular weight of approximately 500 Daltons, and which have the chemical structure that is selected from the formulas shown below as Formulas 1 through 10.

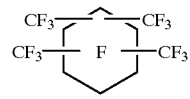

Formula 1

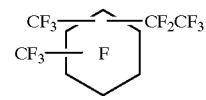

Formula 2

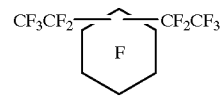

Formula 3

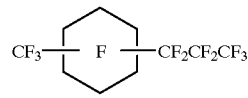

Formula 4

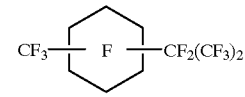

Formula 5

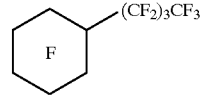

Formula 6

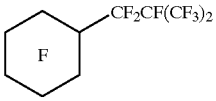

Formula 7

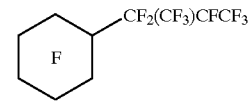

Formula 8

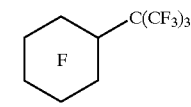

Formula 9

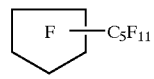

Formula 10

In the Formulas 1–10 the symbol F in the center of the 5 or 6 membered ring represents that all hydrogens of the corresponding cyclohexane or cyclopentane ring have been replaced with fluorine. In other words, F represents that the ring is perfluorinated. The formulas represent all possible positional, stereo (such as cis and trans) and optical isomers (enantiomers) of the compounds depicted in the formulas. In Formula 10 the symbol $C_5F_{11}*$ represents not only a perfluorinated pentyl moiety, but any combination of perfluorinated alkyl groups where in the perfluorinated alkyl groups the total number of carbons is 5 and the total number of fluorines is 11. In other words and by way of example in Formula 10 the symbol $C_5F_{11}*$ represents a $CF_3$ group in combination with a perfluorinated n-butyl, sec-butyl, isobutyl or t-butyl group, or five $CF_3$ groups, or combination of a perfluorinated ethyl group with a perfluorinated n-propyl or iso-propyl group, etc. Moreover, Formula 10 also represents all possible positional, stereo and optical isomers of these compounds.

The perfluorinated compounds utilized in accordance with the invention as a gas exchange medium in liquid ventilation and in artificial blood are liquids at ambient temperature and have a vapor pressure at physiological temperature such that the use of these compounds does not result in the development of hyperinflated non-collapsible lung syndrome. Moreover, the vapor pressure and therefore the rate of evaporation/exhalation from the lungs of these perfluorinated compounds is still sufficiently high so that the compounds are satisfactorily cleared from the lungs after use of the compounds (treatment) is discontinued. The boiling point of the compounds is in the range of approximately 144 to 146° C. Preferably those specific perfluorinated compounds are used in accordance with the invention which either can exist only in a single isomeric form and can be purified from other contaminants to attain a pure or substantially pure state, or which, although capable of existing in more than one isomeric form, can be readily purified to attain isomeric purity.

BRIEF DESCRIPTION OF THE DRAWING

FIG. 1 is a graph showing the rate of exhalation of F-1,2,3,5-tetramethylcyclohexane and of F 1-methyl-4-isopropylcyclohexane (F-menthane) from the rat.

DETAILED DESCRIPTION OF THE INVENTION

DESCRIPTION OF THE PREFERRED EMBODIMENTS

The following specification taken in conjunction with the drawings sets forth the preferred embodiments of the present invention. The embodiments of the invention disclosed herein are the best modes contemplated by the inventors for carrying out their invention, although it should be understood that various modifications can be accomplished within the parameters of the present invention.

Referring to the Formulas 1–9 shown in the Summary section of the present application, it will be apparent to those skilled in the art that these formulas represent perfluorinated cyclohexane derivatives which have perfluoroalkyl substituents having a total of 4 carbons in the alkyl groups. The term "perfluoro" in this regard has the meaning generally accepted in the art, namely it means that all hydrogens of the hydrocarbon skeleton have been replaced with a fluoro atom. It is well known in the art that perfluorinated hydrocarbons, including the ones used in accordance with the present invention, are biologically inert, non-toxic and as far as is presently known they do not undergo metabolic or catabolic transformation in any known mammal. In addition to their inertness, an important property of these compounds which enables them to be utilized as a medium of biological gas exchange is their ability to dissolve a large quantity of gases, including oxygen and carbon dioxide.

Formulas 1 through 9 represent all possible positional and stero isomers of the perfluorinated cyclohexyl derivatives having the empirical formula $C_{10}F_{20}$. Those skilled in the art will readily understand that numerous positional isomers exist. For example, the tetratrifluoromethyl compounds depicted in Formula 1 can be the following positional isomers: perfluoro 1,2,3,4 tetramethylcyclohexane, perfluoro-1,2,4,5-tetramethylcyclohexane and perfluoro 1,2,3,5 tetramethylcyclohexane. For brevity of description the "perfluoro state" of a compound is sometimes indicated here with the symbol "F". Thus, perfluoro 1,2,3,4 tetramethylcyclohexane can also be written as "F 1,2,3,4 tetramethylcyclohexane". For the compounds shown in Formula 2 the following positional isomers are possible: F 1,2-dimethyl-3-ethylcyclohexane, F 1,2-dimethyl-4-ethylcyclohexane, F 1,3-dimethyl-2-ethylcyclohexane, F 1,3-dimethyl-4-ethylcyclohexane, F 1,3-dimethyl-5-ethylcyclohexane and F 1,4-dimethyl-2-ethylcyclohexane. For each of the disubstituted cyclohexanes shown in Formulas 3, 4 and 5 three positional isomers are possible, these are where the substituents are in 1,2, 1,3 or in the 1,4 (ortho, meta or para) positions.

Because of the nature of the cyclohexane ring depicted in Formulas 1–9, and of the cyclopentane ring depicted in Formula 10, cis and trans isomerism (stereoisomerism) and even optical isomerism also exists among the compounds of these formulas, so that the formulas encompass a relatively large number of positional isomers, stereoisomers and for those compounds which include an assymetric or chiral center, optical isomers as well. For example, each of the disubstituted compounds depicted in Formulas 3, 4 and 5 can exist either as cis or as a trans isomer. Therefore, Formulas 3, 4 and 5 represent a total of 18 different chemical entities not counting possible optical isomers (enantiomers) nor diastereomers.

However, it is generally known in the art that compounds of the same molecular weight and of the same type of general structure tend to have similar vapor pressure versus temparature profiles. Vapor pressure is difficult to measure directly, however, it is well known that the boiling temperature of a liquid is directly related to its volatility or vapor pressure. Therefore, compounds of the same molecular weight and of similar structure tend to have same or closely related boiling temperatures. This is known to be particularly true in the field of perfluorocarbons. Among the compounds within the scope of the present invention boiling temperatures measured at atmospheric pressure have become available for the following specific compounds:

F-1-ethyl-2,4-dimethylcyclohexane b.p. 146° C.;
F-1,2,4,5-tetramethylcyclohexane b.p. 146° C.;
F-1,2,3,5-tetramethylcyclohexane b.p. 146° C.;
F-1-methyl-4-isopropylcyclohexane b.p. 144° C., and
F-n-butylcyclohexane b.p. 145° C.

As can be seen, the boiling points of the above-noted exemplary compounds, and by analogy of all compounds within the scope of the present invention, are well within the range (approximately 142 to 160° C.) that is generally considered well suited for compounds utilized as gas exchange medium in liquid ventilation and/or in artificial blood. Perfluoro compounds within this range do not cause hyperinflated lung syndrome, and are transpired from the mammalian body by evaporation/exhalation at an acceptable rate. However, the compounds do not evaporate so rapidly during treatment that undue replenishment would be required.

Because measuring boiling points at atmospheric pressure can be difficult or cumbersome, especially when relatively small samples of the liquid are available, a more feasible method has been devised in accordance with the present invention to measure the "volatility" of a liquid. In accordance with this method, which is described in more detail below in the experimental section of this application for patent, the compound to be measured (subject compound) is mixed with a known (preferably equal) quantity of a reference perfluorocarbon the volatility (boiling temperature and/ or vapor pressure versus temperature profile) of which is known. A reference compound conveniently employed for this purpose is F-cis-decalin which at atmospheric pressure has a boiling point of 141° C. The mixture of the two liquids is maintained in a closed container and the "headspace" above the liquids is allowed to equilibrate with the liquid below. A sample of the saturated gas mixture in the "headspace" is then withdrawn and is analyzed by chromatography to determine the ratios of the two components in the saturated gas mixture. If the two compounds had the same vapor pressure at the temperature of the measurement (usually ambient temperature) then the quantities of the compounds in the saturated gas mixture would also be equal, provided the liquids were mixed in equal quantities. Thus, the ratios of the two components in the saturated gas mixture in the headspace provide a measure of the volatility/vapor pressure of the liquid to be tested, and provide a basis for extrapolation to obtain a boiling point at atmospheric pressure.

"Headspace" saturated gas ratio experiments described in principle above, and detailed below, demonstrated that all 5 exemplary $C_{10}F_{20}$ perfluorocarbons in accordance with the invention have significantly lower vapor pressure at ambient temperature than F-cis decalin, signaling that the use of these compounds in liquid ventilation and artificial blood would not cause hyperinflated lung syndrome.

$C_{10}F_{20}$ perfluorocarbons which are preferably used in accordance with the present invention are selected from among the compounds represented by Formulas 1–10 with a view to attaining pure or substantially pure substances substantially free of isomers. This is important for practical purposes because it is well known that isomeric compounds, whether they are positional isomers or stereoisomers (such as cis, trans or diastereomers) are often difficult to separate in substantial quantities. Whereas present day sophisticated analytical techniques, such as gas chromatography (GC) or high pressure liquid chromatography (HPLC) can often detect the presence of isomers in a substance, separation of the isomers on a preparative scale is often a more difficult task. Moreover, pertinent laws and regulations by the agencies which permit the use of drugs or related pharmaceuticals in therapy or even experimental use in humans, require certain levels of purity and knowledge of the composition of the substances or compounds to be used. It is much more time consuming and expensive to carry a mixture of isomeric compounds through the appropriate phases of testing in animals and humans, until regulatory approval is obtained, than it is to do the same with pure "single chemical entity" substances. In addition, even during manufacturing and testing phases, quality control of a mixture of isomers is often more difficult than with a single entity compound.

For the foregoing and related reasons, use of the following compounds in liquid ventilation and artificial blood is preferred in accordance with the present invention:

F-n-butylcyclohexane (Formula 6);
F-(2-methylpropyl)cyclohexane (Formula 7, iso-butyl);
F-(1-methylpropyl)cyclohexane (Formula 8, sec-butyl);
F-t-butylcyclohexane (Formula 9);
F-1,1-diethylcyclohexane (Formula 11);
F-1-methyl-1-n-propylcyclohexane (Formula 12);
F-1-methyl-1-iso-propylcyclohexane (Formula 13);
F-1-pentylcyclopentane (Formula 14);
F-1-methyl-1-butylcyclopentane (Formula 15);
F-1-ethyl-1-propylcyclopentane (Formula 16).

In Formulas 14, 15, and 16 the pentyl, butyl and propyl groups represent all possible positional isomers of said groups, for example "propyl" represents n-propyl and iso-propyl as well, and "butyl" represents n-butyl, t-butyl and 1-methylpropyl and 2-methylpropyl groups. However, only the use of single chemical entitles, not the use of mixtures, is preferred.

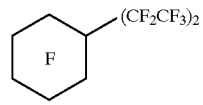

Formula 11

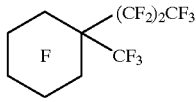

Formula 12

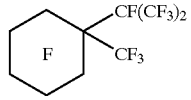

Formula 13

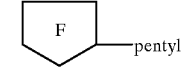

Formula 14

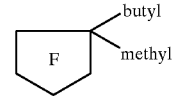

Formula 15

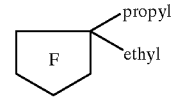

Formula 16

As it can be readily ascertained from their chemical structure, the preferred compounds of Formulas 6–9 and 11–16 are single positional isomers and cis and trans isomerism for these compounds is not possible. The compound of Formula 8 and some of the compounds within the scope of Formulas 14 and 15 have one or more chiral centers and therefore exist in enantiomeric and some in diastereomeric forms. Enantiomers, however are not expected to give rise in the testing and regulatory approval process to problems of the same magnitude as positional isomers, because a racemic mixture of compounds is often considered acceptable for regulatory purposes. Also in chromatographic and many other analytical techniques, unless the chromatography involves a "chiral column", a racemic mixture is not resolved.

The $C_{10}F_{20}$ compounds which are presently most preferred in accordance with the present invention are:

F-t-butylcylohexane (Formula 9);
F-1,1-diethylcyclohexane (Formula 11), and
F-neopentylcyclopentane (Formula 17)

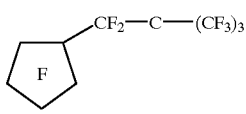

Formula 17

The $C_{10}F_{20}$ compounds used within the scope of the present invention, and particularly the preferred compounds shown in Formulas 6–9 and 11–16 can be synthesized from homologous hydrocarbons by well-known techniques, such as reaction with cobalt trifluoride in a furnace. A method of manufacture of F-tertiary-butylcyclohexane is described in U.S. Pat. No. 4,453,028, incorporated herein by reference. Further procedures for the synthesis of $C_{10}F_{20}$ cyclohexane derivatives are described in U.S. Pat. Nos. 5,300,528, 4,105, 798, and 5,093,432 which are also specifically incorporated herein by reference. Generally speaking the synthesis of perfluorocarbons is described in detail in the book "Chemistry of Organic Fluorine Compounds II. A Critical Review". Edited by Milos Hudlicky and Attila E. Pavlath, published by the American Chemical Society (1995), incorporated herein by reference. The basic technique for cobalt trifluoride fluorination is set forth in U.S. Pat. No. 2,631,170. The basic technique of liquid phase fluorination using diluted fluorine gas is set forth in U.S. Pat. No. 5,093,432. U.S. Pat. Nos. 2,631,170 and 5,093,432 are incorporated herein by reference.

In accordance with the present invention, the $C_{10}F_{20}$ compounds, and particularly the preferred embodiments of Formulas 6–9 and 11–16 and still more particularly the most preferred embodiments, are utilized as medium of gas exchange in liquid breathing and in artificial blood. These mediums of gas exchange can be employed in accordance with the present state of the art, namely in "total" or "tidal" liquid ventilation, "partial" liquid ventilation and in "low volume" (alvolear) ventilation as well. For example, the compounds selected in accordance with the present invention can be used to fill the "pulmonary functional residual capacity" of a mammal, in accordance with the methods and apparatus described in U.S. Pat. No. 5,437,272 (Fuhrman) which is incorporated herein by reference. A recently issued United States Patent by one of the present inventors U.S. Pat. No. 5,674,913 describes a method of assisting normal breathing in a mammal having a lung disorder, by introducing a perfluorocarbon into the alveolar sacs of the lung through the trachea. The perfluorocarbons selected in accordance with the present invention can also be used in the method of said application. U.S. Pat. No. 5,674,913 is also incorporated herein by reference. As a medium of gas exchange in artificial blood the compounds can be used for example as described in U.S. Pat. No. Re: 33,451 (incorporated herein by reference) and as is generally known in the state-of-the-art.

The $C_{10}F_{20}$ compounds, and particularly examples of the preferred embodiments of Formulas 6–9 and 11–16 selected for use as a medium of gas exchange in accordance with the present invention do not cause hyperinflated lung syndrome in experimental animals (rabbit and baboon) and are exhaled from the body at an acceptable rate. The ensuing "specific embodiments" (experimental) section of this application describes the animal testing conducted with examplary compounds, and also experiments wherein the volatility of the compounds selected in accordance with the invention was measured.

Description of Animal Tests and Volatility Measurements
Animal testing is performed in accordance with Protocols 1, 2, 3 and 4, which are described below.
PROTOCOL 1: Intratracheal Administration of Perfluorocarbon Neat Liquids to Rats With Survival This protocol is especially useful for the accurate administration of perfluorocarbon neat liquids to the lungs of small animals through a Silastic catheter inserted in the trachea through a tracheotomy. The following protocol and example are specific for rats of the genus Rattus, bred for use in research. Adult Sprague Dawley female rats are normally used.

The nonfasted rat is weighted and anesthetized with a volatile anesthetic such as enflurane, halothane or similar agent. Surgical plane anesthesia is achieved using an intraperitoneal injection of ketamine hydrochloride in saline (25 mg/ml), at an initial dose of 80 mg/kg. Additional injections of about 20 mg/kg are given as needed to ensure appropriate anesthesia. A single subcutaneous injection of chlorpromazine in saline (25 mg/ml), as a dose of 5 mg/kg, is used for muscle relaxation. The neck area is shaved, and the skin is cleaned with 70% alcohol and scrubbed with betadine.

The rat is positioned on her back on a padded surgical platform, and humidified 100% oxygen is administered through a mask loosely covering the rat's head. Core temperature is monitored using a small animal rectal Telethermometer probe and meter from Yellow Springs Instruments, Co. A heat lamp is used to maintain body temperature between 35 and 37 degrees Celsius.

Sterilized instruments are used for the surgical procedure. A 2 cm midline incision is made in the neck over the trachea. The underlying fat and muscle is dissected to expose the trachea. A narrow piece of sterile umbilical tape is passed beneath the trachea and a small hole is made between rings, below the thyroid, using a 21 gauge needle. The hole is enlarged with the scalpel, if needed, to accommodate the Silastic catheter. This Silastic catheter, either single or double lumen and fitted with a 23 gauge tubing adapter, is then inserted about 1 cm into the trachea. The oxygen flow is now directed into, and around, the catheter instead of into the mask.

The surgical platform is elevated about 30–40° to facilitate the gravity flow of perfluorocarbon neat liquid into the lungs. The perfluorocarbon neat liquid is then slowly delivered through the catheter from a glass syringe attached to the tubing adapter, at a rate of about 1 ml per minute. Oxygen is concomitantly delivered. The rat can also be rotated to the left and right during dosing to help distribute the liquid. Perfluorocarbon neat liquid doses up to 20 ml/kg have been infused into the lungs by this method. The tracheal catheter is removed, and the board lowered so that the head and neck are kept slightly above the chest to allow any perfluorocarbon neat liquid in the trachea to drain into the lungs. The small opening in the trachea is closed using a single suture of 5-0 silk, as is the muscle layer. The skin is closed with continuous sutures of 4-0 silk. The rat is then kept on humidified 100% oxygen using the mask, and observed until recovery, when it is returned to its cage in the colony.
PROTOCOL 2: Intratracheal Administration of Perfluorocarbon Neat Liquids to Rabbits With Survival 1. The fasted animal is sedated with 2.5 mg/kg subcutaneous chlorpromazine (25 mg/ml).

2. Approximately 30 minutes later the animal is gently restrained and the necessary ear blood vessels catheterized with Teflon catheters, such as an Abbocath T-22 Gaxl ¼", fitted with a 3-way stopcock. Topical 2% Lidocaine may facilitate the cannulation.

3. The animal is anesthetized with intravenous sodium pentobarbital (30 mg/ml in normal saline) at a dose of 30 mg/kg.

4. The throat is shaved and disinfected with 70% ethyl alcohol and Betadine.

5. The area of the incision is filtrated with 2% Lidocaine.

6. With the animal lying on its back, a 1–2' midline incision is made over the trachea below the laryngeal prominence.

7. The muscle is incised and the area around the trachea is blunt dissected.

8. A length of sterile umbilical tape is passed beneath the trachea to help isolate it and to secure the tracheal cannula.

9. The trachea is then cut between rings and a sterilized Silastic tube (5 mm OD) is inserted in the trachea to a point above the bronchial bifurcation.

10. The head and shoulders of the animal are elevated for gravity administration of the perfluorocarbon neat liquid. The perfluorocarbon neat liquid is filtered through a sterile, 0.22 micron filter during administration.

11. The Silastic tracheal cannula is removed and the trachea closed with two sutures of 5-0 silk.

10. A small piece of Gelfoam is placed over the tracheal incision and the muscle and skin are closed with 4-0 silk.

The animal is administered humidified, 100% oxygen during the entire procedure and small maintenance doses of intravenous sodium pentobarbital are given when needed.

PROTOCOL 3: Gas Chromatographic Determination of the Exhalation Rate From Rats Having Perfluorocarbon Neat Liquid in the Lungs The rat is placed in a specially designed chamber consisting of a perforated ceramic disk in a 1 liter Pyrex glass dissicator with an oxygen inlet and outlet, and a typical oxygen flow rate of 600 ml/min. A magnetic stirring bar below the disk stirs the atmosphere in the dessicator, which has a cover sealed with glycerol.

After 20 minutes of equilibration, the gas flow from the outlet of the rat chamber is measured using a Humonics Optiflow 650 digital flowmeter. Samples are then taken from the flow outlet for GC analysis using a Hamilton side port needle syringe.

Samples taken from the outlet are injected onto a 20 foot long×⅛ inch stainless steel packed column (30% SE30 on Chromsorb PAW 80/100 mesh) in a Hewlett Packard 5890 GC. Head pressure of the 5% methane in argon carrier gas is maintained at 50 pounds/square inch, with an end flow rate of 25 milliliters/minute. Quantitive measurement is accomplished with an electron capture detector. All data is collected and stored using a Hewlett Packard chemstation data system.

Quantitation is done by comparison of the measured value of the rat's exhalation to a known standard. The standard is prepared by injecting a 0.1 to 2 microliter ($\mu$L) aliquot of perfluorocarbon neat liquid into a sealed 120 milliter (mL) serum vial. It is allowed to stand at room temperature for at least one hour to completely volatilize. This is referred to as the "Stock standard". A 120 $\mu$L aliquot of the stock standard vapor is taken and injected into a second sealed 120 mL serum vial, producing a 1000:1 dilution of the original; this is referred to as the "working standard". Accurately measured volumes of the working standard, or the oxygen carrier gas from the rat chamber, are alternately injected onto the GC instrument for quantitation.

Calculation of the rate of exhalation is performed using the peak height (or area) from the chromatogram of the rat's breath, the peak height (or area) from the chromatogram of the working standard, the known concentration of the working standard, and the oxygen flow rate through the chamber to give the exhalation rate of the fluorocarbon vapor as microliters of fluorocarbon per day.

FIG. 1 of the appended drawings shows the rate of exhalation of F-1,2,3,5-tetramethylcyclohexane and of F 1-ethyl-4-isopropylcyclohexane (F-menthane) in the rat, substantially as determined in accordance with Protocol 3. Both of these compounds are $C_{10}F_{20}$ perfluorocarbons the use of which in liquid ventilation is within the scope of the present invention. As it was discussed above, the boiling points of these compounds for practical purposes are virtually the same or very close to the boiling points of all of the perfluorocarbons which are utilized in liquid ventilation and artificial blood in accordance with the present invention. The rate of exhalation indicated in the graph for both of these $C_{10}F_{20}$ perfluoro compounds is considered acceptable, and indicates that undue exposure of the animal to potential long term effect of the perfluorocarbon is likely to be avoided.

PROTOCOL 4: Test of Intratracheal Neat Liquid Perfluorocarbons for Pulmonary Hyperinflation in the Rabbit Fasted, healthy, Pasteurella-free, young adult female New Zealand white rabbits weighing about 1.8 to 2.2 kilograms, were used. The rabbits were sedated with chlorpromazine, anesthetized with a mixture of ketamine and xylazine, and supported by oxygen breathing. The trachea was cannulated with a soft, sterile Silastic tube stabilized in place with umbilical tape. Filtered, neat liquid fluorocarbon (medical grade) was administered slowly in the doses shown in the table. The cannula was removed, the incision closed and the animal allowed to recover in USDA-approved, air conditioned quarters. The rabbits were observed frequently until sacrifice on the fourth day after infusion.

Results of tests conducted substantially as described in Protocol 4, with F-1-ethyl-2,4-dimethylcyclohexane (b.p. 146° C.) and F-1,2,4,5-tetramethylcyclohexane (b.p. 146° C.) caused no pulmonary hyperinflation in the rabbit, whereas F-cis-decalin (b.p. 142.5 C.) did. These results are summarized below in Table 1 where the dose of the respective fluorcarbons and the number of animals involved in the test are also indicated.

TABLE 1

Tests of intratracheal neat liquid perfluorocarbons for pulmonary hyperinflation in the rabbit.

| Perfluorocarbon Neat Liquid | Dose (cc/kg) | Number of Animals | Hyperinflation |
| --- | --- | --- | --- |
| F-ethyldimethylcyclohexane | 4 | 2 | None |
| F-1,2,4,5-tetramethylcyclohexane | 4 | 2 | None |
| F-1,2,4,5-tetramethylcyclohexane | 6 | 2 | None |
| F-1,2,4,5-tetramethylcyclohexane | 8 | 2 | None |
| F-1,2,4,5-tetramethylcyclohexane | 10 | 1 | None |
| F-decalin | 4 | 2 | Moderate |
| F-decalin | 6 | 2 | Moderate |
| F-decalin | 8 | 2 | Severe* |
| F-decalin | 10 | 1 | Moderate |

* Both rabbits died in the morning of the fourth day, shortly after being removed from their cages.

By way of further description of the tests summarized in Table 1 it is noted that several of the animals which received the F-decalin showed signs of pulmonary distress by the second day. These symptoms included rapid and noticeably labored breathing, and, in general, these animals appeared to be hypoxic and hypercapnic. At necropsy the F-decalin lungs were pale pink and showed various degrees of hyperinflation. The animals which received the F-1,2,4,5-tetramethylcyclohexane and the F-ethyldimethyl-cyclohexane showed no signs of distress. At necropsy their lungs were found to be normal in appearance and were not hyperinflated.

Test of Intratracheal Neat Liquid Perflurocarbons for Pulmonary Hyperinflation in the Baboon To determine if F-1-ethyl-4,4-dimethylcyclohexane caused hyperinflation in the non-human primate, two fasted, normal, healthy juvenile female baboons weighing about 3.5 to 5 kilograms were given intratracheal neat liquid. An IACUC-approved protocol was followed. The procedure, similar to the description in Protocol 4 was performed under sterile conditions in a USDA-approved primate facility. One baboon received 2 cc/kg and the other 4 cc/kg of F 1-ethyl-2,4-dimethylcyclohexane via tracheal cannula. Both animals were observed frequently, and no untoward reactions were observed during, or in the days following, the infusion. The animals gained weight, and behaved in a normal fashion in their quarters. Both were sacrificed ten weeks after the infusion. At necropsy their lungs were found to be normal in appearance and were not hyperinflated. Laboratory examination of the lung sections revealed no abnormalities.

Measurements Comparing the Vapor Phase Concentrations of Certain Perfluoroalkylcyclohexanes ($C_{10}F_{20}$) and Cis Perfluorodecalin ($C_{10}F_{18}$) With the Liquid Phase Concentration Using Gas Chromatography and Electron Capture Detection A volume (200 microliters) of the perfluorinated liquid under study was mixed with an equal volume of the cis isomer of F-decalin (BP=142.5° C.). A stock standard of this mixture was prepared by evaporating two microliters of the liquid in a 120 milliliter glass serum vial sealed with a rubber septum and aluminum cap. This volume was chosen so that complete evaporation of the liquid could take place. After volatilization, this stock standard was diluted by transferring 120 microliteres of the vapor to a clean, sealed 120 milliliter serum vial to make the working standard. A 20 microliter sample of the working standard was analyzed using a Hewlett-Packard 5880A gas chromatograph with electron capture detector and column temperature at 80° C. The chromatogram and peak heights were recorded and printed using Hewlett-Packard ChemStation software. This enabled calibration of the electron capture detector for each of the $C_{10}F_{20}$ compounds tested, and the known concentration in the liquid phase could be used to determine the relative sensitivity, $R_1$ in the table, of the detector to the perfluorinates being used.

To obtain the relative concentrations of the perfluorinates in the saturated vapor phase, 30 microliters of the headspace vapor over the 50/50 liquid mixture was diluted in a clean, sealed 120 milliliter serum vial. A 20 microliter sample of this diluted headspace was analyzed on the gas chromatograph. The sample volumes and dilutions were selected so that the F-cis-decalin peaks in the working standard and diluted headspace were of similar height in order to avoid any potential problems with a non-linear detector response. The peak height ratio in the vapor phase, $R_2$, was corrected for sensitivity by dividing by $R_1$, to give the relative concentration of the $C_{10}F_{20}$ compound to the F-cis-decalin, R2/R1, in the headspace over the liquid; a comparison of the vapor pressures of the liquids in the mixture.

TABLE 2

Direct comparison of the vapor phase concentrations of certain perfluoro-alkylcyclohexanes ($C_{10}F_{20}$) and cis-perfluorodecalin ($C_{10}F_{18}$) with the liquid phase concentration using gas cromatography and electron capture detection.

| Liquid Phase Peak Heights (thousands) in working standard | | Peak Height Ratio cis-decalin/$C_{10}F_{20}$ | Vapor Phase Peak Heights (thousands) in diluted headspace | | Peak Height Ratio cis-decalin/$C_{10}F_{20}$ | Fraction of $C_{10}F_{20}$ in vapor phase |
|---|---|---|---|---|---|---|
| cis-decalin | $C_{10}F_{20}$ | $R_1$ | cis-decalin | $C_{10}F_{20}$ | $R_2$ | $R_2/R_1$ |
| 39.5 | 41.5[1] | 1.05[1] | 38.7 | 35.4[1] | 0.91[1] | 0.87[1] |
| 39.2 | 22.2[2] | 0.57[2] | 41.5 | 18.2[2] | 0.44[2] | 0.77[2] |
| 37.9 | 24.9[3] | 0.66[3] | 39.6 | 19.5[3] | 0.49[3] | 0.74[3] |
| 34.4 | 21.8[4] | 0.63[4] | 41.6 | 23.2[4] | 0.56[4] | 0.89[4] |
| 37.2 | 57.3[5] | 1.54[5] | 45.3 | 59.15[5] | 1.30[5] | 0.84[5] |

[1] F ethyl-2,4-dimethylcyclohexane
[2] F 1,2,4,5-tetramethylcyclohexane
[3] F 1,3,4,5-tetramethylcyclohexane
[4] F 1-methyl-4-isopropylcyclohexane
[5] F n-butylcyclohexane Table 2 above shows the results obtained with five separate $C_{10}F_{20}$ perfluorocarbons that are utilized in accordance with the present invention. The chemical name of each of the perfluorocarbons measured is indicated by the superscripts over the numerical data. The data of Table 2 clearly demonstrate that the vapor pressure of the 5 $C_{10}F_{20}$ compounds are significantly lower than that of F cis decalin.

What is claimed is:

1. A method of facilitating transport of gases in a biological system, comprising using as a medium of gas transport a perfluorocarbon liquid which is selected from the formulas 20 through 32, wherein said formulas 20 through 32 consist of Formula 20
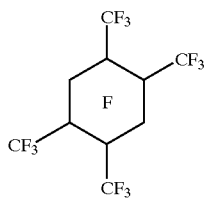

Formula 21
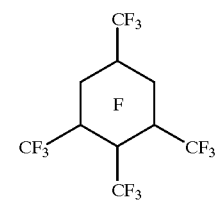

Formula 22
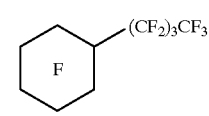

Formula 23
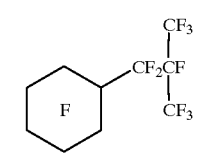

Formula 24
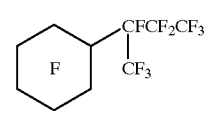

Formula 25
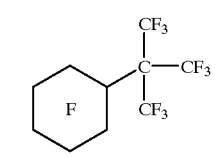

Formula 26
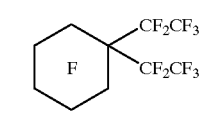

Formula 27
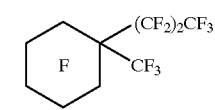

Formula 28
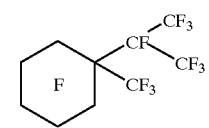

Formula 29
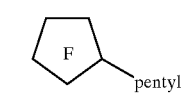

Formula 30
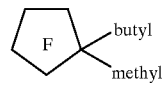

Formula 31
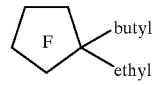

Formula 32
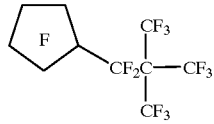

where in the formulas the terms pentyl, butyl, propyl, ethyl and methyl represent the respective perfluorinated alkyl groups, and chosen based on their capability for stereoisomer purity.

2. The method in accordance with claim 1 where the perfluorocarbon has the structure of formula 20.

3. The method in accordance with claim 1 where the perfluorocarbon has the structure of formula 21.

4. The method in accordance with claim 1 where the perfluorocarbon has the structure of formula 22.

5. The method in accordance with claim 1 where the perfluorocarbon has the structure of formula 23.

6. The method in accordance with claim 1 where the perfluorocarbon has the structure of formula 24.

7. The method in accordance with claim 1 where the perfluorocarbon has the structure of formula 25.

8. The method in accordance with claim 1 where the perfluorocarbon has the structure of formula 26.

9. The method in accordance with claim 1 where the perfluorocarbon has the structure of formula 27.

10. The method in accordance with claim 1 where the perfluorocarbon has the structure of formula 28.

11. The method in accordance with claim 1 where the perfluorocarbon has the structure of formula 29.

12. The method in accordance with claim 1 where the perfluorocarbon has the structure of formula 30.

13. The method in accordance with claim 1 where the perfluorocarbon has the structure of formula 31.

14. The method in accordance with claim 1 where the perfluorocarbon has the structure of formula 32.

15. The method in accordance with claim 1 comprising the step of assisting breathing in a mammal in need of such assistance by introducing into the lungs of the mammal a perfluorocarbon liquid in accordance with claim 1.

16. The method in accordance with claim 15 where a tidal volume quantity of perfluorocarbon liquid is introduced into the lungs of the mammal.

17. The method in accordance with claim 15 where a quantity of perfluorocarbon is instilled into the lungs of the mammal to fill the functional residual volume of the lungs.

18. The method in accordance with claim 15 where a quantity of perfluorocarbon is instilled into the lungs of the mammal to fill the alveoli of the lungs.

* * * * *

UNITED STATES PATENT AND TRADEMARK OFFICE
CERTIFICATE OF CORRECTION

PATENT NO.   : 6,167,887 B1
DATED        : January 2, 2001
INVENTOR(S)  : Clark et al.

It is certified that error appears in the above-identified patent and that said Letters Patent is hereby corrected as shown below:

Column 4,
Line 35, Formula 5  should be 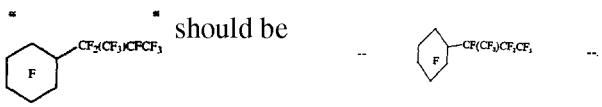

Line 49, Formua 8  should be

Line 59, Formula 10 insert -- * -- after "$F_{11}$"

Column 16,
Line 8, Formula 31, "butyl" should be -- propyl --.

Signed and Sealed this

Sixth Day of August, 2002

*Attest:*

*Attesting Officer*

JAMES E. ROGAN
*Director of the United States Patent and Trademark Office*